United States Patent
Farmerie et al.

(10) Patent No.: US 6,315,910 B2
(45) Date of Patent: *Nov. 13, 2001

(54) METHOD FOR CONTROLLING SNAILS USING DIALKYL DIALLYL AMMONIUM POLYMERS

(75) Inventors: James E. Farmerie, Wexford, PA (US); James K. Dicksa, Antioch, CA (US)

(73) Assignee: Calgon Corporation, Pittsburgh, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,791

(22) Filed: Mar. 3, 1999

Related U.S. Application Data

(60) Provisional application No. 60/077,495, filed on Mar. 11, 1998.

(51) Int. Cl.[7] .......................................................... C02F 1/50
(52) U.S. Cl. ........................... 210/755; 210/749; 210/764; 514/642
(58) Field of Search .................................. 210/698, 701, 210/755, 764, 749; 514/642

(56) References Cited

U.S. PATENT DOCUMENTS

| | | | | |
|---|---|---|---|---|
| 4,462,914 | * | 7/1984 | Smith | 210/755 |
| 4,816,163 | * | 3/1989 | Lyons et al. | 210/698 |
| 4,857,209 | * | 8/1989 | Lyons et al. | 210/755 |
| 5,015,395 | * | 5/1991 | Muia et al. | 210/755 |
| 5,062,967 | * | 11/1991 | Muia et al. | 210/755 |
| 5,096,601 | * | 3/1992 | Muai et al. | 210/755 |
| 5,192,451 | * | 3/1993 | Gill | 210/755 |
| 5,900,157 | * | 5/1999 | Petrille et al. | 210/755 |

* cited by examiner

*Primary Examiner*—David A. Simmons
*Assistant Examiner*—Frank M. Lawrence
(74) *Attorney, Agent, or Firm*—Diane R. Meyers; Daniel P. Cillo; Eckert Seamans Cherin & Mellott, LLC

(57) ABSTRACT

A method for controlling snails in aqueous systems which involves treating aqueous systems which contain snails or which are prone to snail infestation with an effective amount of a water-soluble dialkyl diallyl quaternary ammonium polymer (polyquat) is disclosed. A preferred polymer is a poly(quaternary ammonium) compound having a recurring structure (DMDAAX$^-$) resulting from the polymerization of monomeric dimethyl diallyl ammonium X$^-$, wherein X$^-$ is any suitable anion.

11 Claims, 1 Drawing Sheet

METHOD FOR CONTROLLING SNAILS USING DIALKYL DIALLYL AMMONIUM POLYMERS

This application claims the benefit of U.S. Provisional Application No. 60/077,495, filed Mar. 11, 1998.

FIELD OF THE INVENTION

The present invention relates to methods for controlling snails in aqueous systems containing snails and/or prone to growth of snails. More specifically, the present invention is directed to such methods for inhibiting both snail growth and development and hatching of snail eggs, wherein the snails and eggs are submerged, partially submerged and/or intermittently submerged in aqueous systems. The methods find particular application in waste water biological treatment systems.

BACKGROUND OF THE INVENTION

Snail infestation has been a problem for some time at waste water treatment facilities. The snails grow and reproduce prolifically in the trickling filter towers and/or nitrification towers of these facilities, and are then carried to the bioflocculation tanks where they accumulate. Snail accumulations of depths up to four feet have been observed in all channels of the bioflocculation tanks. As the snail shells are pulverized they pass into the secondary clarifiers degrading the quality of the effluent. Eventually, the shells get into the digesters and contribute to grit buildup. Waste water treatment systems have problems with the snails grazing on nitrifying bacteria, that is, eating the microbiological fauna. This fauna provides secondary treatment of suspended solids (SS) and reduces biochemical oxygen demand (BOD); elimination of this fauna, therefore, interferes with the nitrification process and causes the effluent to be in violation of discharge permits.

An example of a particular snail that is a problem is one that belongs to the genus Physa or Physella. These organisms are freshwater snails that need a moist environment and can live submerged. These snails are hermaphroditic and capable of self-fertilization. They lay egg cases once or twice per year and die after spawning is completed. Their normal life span is one year. There is about a three week incubation period before juvenile snails appear. Juveniles go directly from the egg to the adult morphology; there is no snail egg larvae stage.

It is known that dialkyl diallyl ammonium polymers, alone or in combination, will kill zebra mussels and larvae in submerged water intake systems as disclosed in U.S. Pat. Nos. 5,015,395; 5,062,967; and 5,096,601, the disclosures of which are incorporated herein in their entirety by reference. Use of these or similar compounds, however, has not been reported in the killing and control of snails in general, or in waste water treatment systems in particular; nor has use of the compound been reported against any other organisms that do not have a larvae stage.

The polymers used in the present methods are used in municipal and industrial water treatment. For example, dimethyl diallyl ammonium chloride polymers are added as clarification aids to the water intakes of municipal potable water plants. To the best of the inventors' knowledge, however, such polymers have not been added to control snail growth or fouling.

Additionally, polyquaternary compounds have been utilized for control of other organisms, such as Asian claims (Corbicula) and microorganisms such as bacteria, fungi, and algae in aqueous systems. See, for example, U.S. Pat. Nos. 4,462,914; 4,113,709 and 4,111,679. Simple quaternary ammonium compounds have been used to control fouling of microorganisms and molluscs. See, for example, Nashimura et al., Japan Kokai No. 74 81,535 (1974); Roth, German Offenlegungsschrift No. 2,642,606; Sindery, French Pat. No. 1,460,037 and McMahon et al., presentation at *American Power Conference*, Chicago, Apr. 23–25 (1990).

Ramsey et al., "Effects of Nonoxidizing Biocides on adult *Corbicula fluminea*" (1988), disclose the use of various biocides, including dodecylguanidine hydrochloride (DGH), benzalkonium chloride, pyridinium chloride, dioctyl dimethyl ammonium chloride, poly[oxyethylene (dimethylamino)-ethylene (dimethylamino)-ethylene dichloride], glutaraldehyde, 2,2-dibromo-3-nitrilo propionamide, N4-dihydroxy-α-oxobenzene ethanimidoyl chloride, 5-chloro-2-methyl-4-isothiazolin-3-one/2-methyl-4-isothiazolin-3-one, N-[(α)-(1-nitroethyl) benzyl] ethylenediamine and 2-(tert-butylamino)4-chloro-6(ethylamine)-5-triazine, to control Asian clams.

U.S. Pat. No. 4,816,163, to Lyons et al., discloses the use of water-soluble alkyl guanidine salts, alone or in combination with methylene bis-thiocyanate or alkyl dimethyl benzyl ammonium chloride, to control the biofouling of macroinvertebrates, particularly Corbicula.

None of the above patents or articles appear to disclose the methods of the present invention.

Current treatment to reduce snail populations is pH adjustment, which is detrimental to the biological organisms in the secondaries. There remains a need, therefore, for methods for controlling snails without affecting the organisms which reduce BOD in the secondary treatment process.

SUMMARY OF THE INVENTION

The methods of the present invention address the above need, by providing methods for controlling snails without affecting the organisms which reduce BOD in the secondary treatment process. The present methods for controlling snails in an aqueous system generally comprise adding to the system an effective amount of a water soluble dialkyl diallyl quaternary ammonium polymer. These methods find particular application in waste water treatment systems, where snails accumulate in nitrification or trickling filter towers and bioflocculation tanks, among other areas.

It is therefore an object of the invention to provide a method for controlling snails in aqueous systems containing snails or prone to growth or contamination of snails.

It is another object to provide a method for controlling the fouling potential of snails in an aqueous system which contains snails or which is prone to growth of snails.

Another object of the current methods is to provide a means for killing snails and inhibiting the development and hatching of snail eggs in a wastewater biological treatment system containing snails.

Yet another object of the invention is to provide a method for killing snails and inhibiting the development and hatching of snail eggs in a wastewater biological treatment system containing snails that are only partially submerged or intermittently submerged.

The above objectives are accomplished by adding to the system to be treated an effective amount of a water soluble dialkyl diallyl quaternary ammonium polymer.

These and other objects of the invention will be apparent to those skilled in the art based upon the following description of the invention and appended claims.

DETAILED DESCRIPTION OF THE INVENTION

Figure 1:
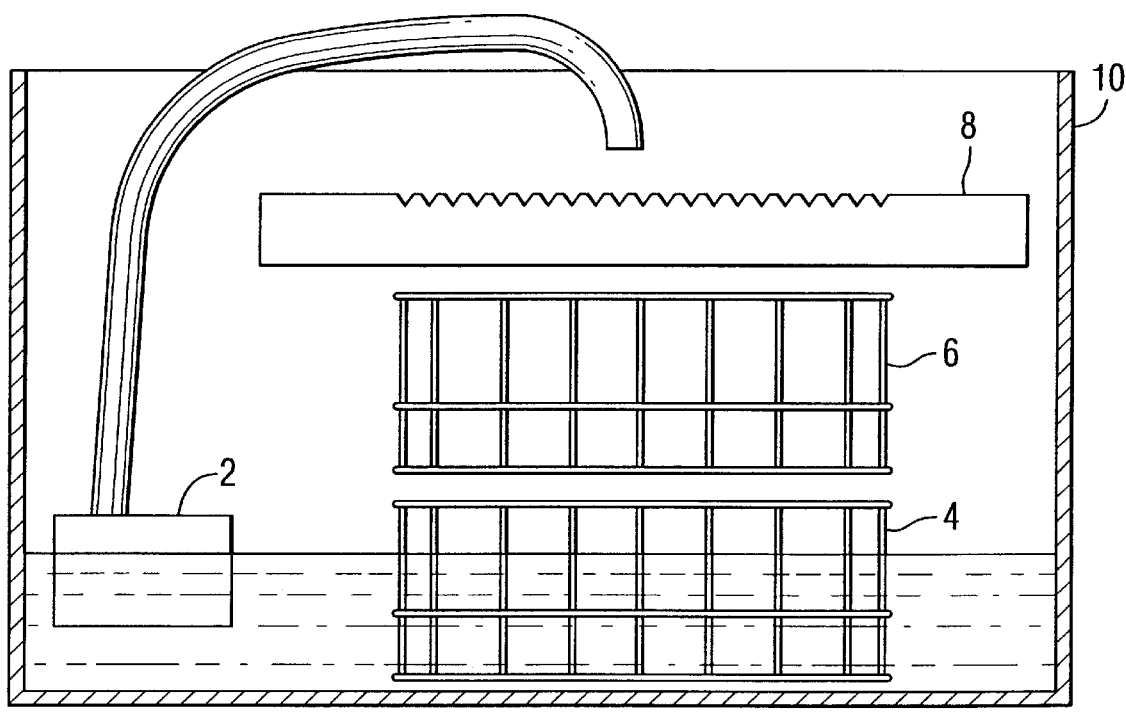
FIG. 1 shows the apparatus used to test the efficacy of the present methods, as described in Example 2.

The present invention is generally directed to a method for controlling snails in an aqueous system comprising adding to the system an effective amount of a water soluble dialkyl diallyl quaternary ammonium polymer ("polyquat"). More than one water soluble dialkyl diallyl quaternary ammonium polymer can be used; other polymers or water treatment products, as described below, can also be used with the dialkyl diallyl quaternary ammonium polymers.

The polyquats used in the present invention comprise quaternary diallyl dialkyl ammonium moieties wherein the alkyl groups are independently selected from alkyl groups of 1 to 18 carbon atoms, preferably $C_{1-4}$ alkyl. Methyl and ethyl are the preferred alkyl groups, and methyl is most preferred. The counterions are selected from the group consisting of conjugate bases of acids having an ionization constant greater than $10^{-13}$, more preferably selected from the group consisting of fluoride, bromide, chloride, hydroxide, nitrate, acetate, hydrogen sulfate, and primary phosphates, and most preferably chloride. The most preferred polyquats are those having the recurring structure: $[DMDAAX^-]$, which represents dimethyl diallyl ammonium $X^-$, wherein the polymer is prepared by polymerizing monomeric dimethyl diallyl ammonium $X^-$, and $X^-$ is any suitable counterion, chloride being most preferred.

Examples of suitable polymers include, but are not limited to, polydimethyl diallyl ammonium chloride (polyDMDAAC), polydiethyl diallyl ammonium chloride (polyDEDAAC), polydimethyl diallyl ammonium bromide (polyDMDAAB), polydiethyl diallyl ammonium bromide (polyDEDAAB) and polydidecyl dimethyl ammonium halide (polyDDAH). PolyDMDAAC's are most preferred. It will be appreciated that use of more than one of these or other polymers is within the scope of the present invention.

The molecular weight of the polymer used is not critical. Generally, however, the weight average molecular weight should range between 500 and about 20,000,000, preferably between about 10,000 and about 10,000,000 and most preferably between about 10,000 and about 3,000,000.

The polyquats used in the present methods may also contain additional moieties. Co- and ter-polymers may be used. For example, polymers containing diethyl diallyl and dimethyl diallyl groups may be used. Additionally, the above diallyl diallyl quaternary ammonium monomers may be polymerized with any suitable monomer, including but not limited to methacryloyloxyethyl trimethyl ammonium chloride (METAC), methacryloyloxyethyl trimethyl ammonium methosulfate (METAMS), methacrylamido propyl trimethyl ammonium chloride (MAPTAC) acryloyloxyethyl trimethyl ammonium chloride (AETAC), acryloyloxyethyl trimethyl ammonium sulfate (AETAMS) and quaternized derivatives of N,N-dimethyl amino ethyl methacrylate, alone or in combination, or polymers made by polymerizing any of the above cationic monomers with acrylamide, methacrylamide or N,N-dimethyl acrylamide. For example, DMDAAC/acrylamide, DMDAAC/METAC, METAMS and/or MAPTAC and DMDAAC/acrylamide/METAC, METAMS and/or MAPTAC polymers can be used.

A wide variety of DMDAAC polymers are commercially available from Calgon Corporation, Pittsburgh, Pa., or the polymers may be prepared using any conventional free radical polymerization technique, such as the technique disclosed by Butler and Angelo, *Journal of American Chemical Society*, Vol. 79, p. 3128 (1957) or the technique suggested in U.S. Reissue Pat. No. Re. 28,543.

A didecyl dimethyl ammonium chloride product is commercially available from Calgon Corporation as H-130. Also, a 50% active, by weight, didecyl dimethyl ammonium chloride is commercially available from Lonza as BARDAC® 2250. This product also contains 10%, by weight, ethanol and 40%, by weight, water.

"Aqueous system" as used herein refers to any aqueous system which contains or is prone to growth of snails. Any such aqueous system can be treated according to the present methods. Particular application is in the treatment of aqueous systems of waste water treatment systems, where snails have been found to accumulate in nitrification towers, trickling filter towers and bioflocculation tanks.

"Snails" is used herein to refer not only to adult snails, but to snail eggs as well. The snails controlled according to the present methods can be submerged, partially submerged, or intermittently submerged in the water of the aqueous system being treated.

"Control" or "controlling" refers collectively to killing snails, inhibiting snail growth, preventing snail growth, inhibiting development and hatching of snail eggs, and controlling the fouling potential of snails.

"Effective amount", as used herein, refers to that amount of polymer necessary to accomplish the purpose of the treatment. The effective amount of water soluble polyquat to use according to the methods of the present invention may vary due to such factors as the ambient temperature of the aqueous system being treated, the presence of substances in the water which bind to or otherwise inactivate cationic polymers (for example, silt), the concentration and predominant state of life cycle of the snail present in the aqueous system to be controlled, the particular polyquat which is employed, and other factors. Generally, however, an effective amount of polyquat will be in the range of from about 0.1 to about 2000 parts per million, preferably about 1 to about 100, more preferably about 5 to 50 parts per million, based on total weight of active polymer added and the total weight of the water in the aqueous system being treated. It will be appreciated that an effective amount for one system may not be an effective amount for another system. For example, while a given amount may be sufficient to control snails in one system, it may not be sufficient to control snails in another. It is within the skill of a water treatment practitioner to determine the effective amount to achieve the desired level of snail control and biological growth for any given system.

It is noteworthy that aqueous systems oftentimes have a "turbidity demand" for cationic polymers. Thus, cationic polymers interact with and are "tied-up" by solids which cause turbidity. For this reason, sufficient polyquat must be fed to both account for the turbidity demand of the system being treated and to control snails. A preferred method therefore comprises: (a) determining the turbidity level of the aqueous system to be treated and the corresponding turbidity demand for the particular polyquat being fed; (b) feeding sufficient polyquat to react with and tie-up the turbidity present, i.e., to account for the turbidity demand of the system by tieing-up existing turbidity; and (c) feeding an effective amount of polyquat to control snails. Preferably, feed steps (b) and (c) can be carried out simultaneously. Step (a) involves routine procedures well within the skill of a water-treatment practitioner.

The cationic polymers employed in the present methods can be added to the aqueous system being treated in any conventional manner and at any point best suited to provide ready dissolution and rapid distribution of the polymer to all points in the aqueous system being treated. Because snails are mobile they can seek shelter in crevices that prevent exposure. The amount of biomass present in the trickling filter, and the concentration of organic matter in the influent, may tie-up the polymer thus preventing contact with the snails. Total submergence of a particular application or piece of equipment is therefore preferred. Feeding of polymer should be continued until the desired level of control is achieved. Depending on various factors such as the size of the system being treated and the severity of the snail problem, daily feeding for a period of one to two weeks may be sufficient.

Various formulations of the polyquat which facilitate its dissolution in water may be prepared in accordance with known methods. Any form of the polyquat can be used, including but not limited to emulsion, solution or dry forms. As noted above, more than one polyquat can be used. Addition of two or more polyquats can be done simultaneously, sequentially or at different times and at different locations during treatment. Also, other water treatment agents can be added to the system being treated in conjunction with the present polyquats. For example, other biocides, surfactants, scale or corrosion inhibitors, dispersants, flocculated or clarification aids can be used with the present polyquats.

The methods of treatment of the present invention will be better understood by the following examples, which illustrate the use of a preferred polyquat to control snails.

EXAMPLES

The following examples are intended to illustrate the present invention and are not intended to limit the invention in any way. All of the polyDMDAAC used in the Examples was provided by Calgon Corporation, Pittsburgh, Pa.

Example 1

Jar testing was also done on snails using primary effluent as the matrix. Twenty snails were added to one liter of primary effluent without any polymer as a control, one liter of primary effluent with 200 ppm of polyDMDAAC, and one liter of primary effluent with 300 ppm of polyDMDAAC. After four hours all control snails were still alive and very active. Snails in the other two jars were inactive and appeared to be dead. All "dead" snails were transferred to fresh effluent to determine if they could recover. After 24 hours, one snail from the 200 ppm jar was alive and active. Thus, the present methods are effective in controlling adult snails.

Example 2

The effectiveness of polyDMDAAC in preventing the development and hatching of snail eggs was evaluated.

Two ten-gallon aquaria were established with an environment similar to that of the trickling filters. Four liters of effluent were added to each tank. FIG. 1 provides an illustration of one tank, 10. A small, submersible pump, 2, was used to circulate the water. Two plastic test tube racks, 4 and 6, were placed in each aquarium to serve as a substrate for microbiological organisms and an attachment site for snail eggs. On top of these racks a plastic blue block, 8, generally used for sludge draining, was placed. This plastic block had numerous slits cut into it and served to disperse the water flowing over it, allowing the water to trickle down onto the racks.

The effluent was allowed to circulate over the racks for approximately one week. Fifty snails were then added to each tank. Three days later, 100 more snails were added to each tank. In this environment the snails will begin to lay egg clusters. The water was changed every other day, with the old water pumped out and fresh effluent added. The tank was assessed for the number of egg clusters present and the approximate number of live snails. Many of the snails used in the example died shortly after laying eggs. As not all of the snails layed eggs during the trial period, live snails also were present. Once at least 20 egg clusters had been laid, chemical addition was initiated.

The experiment was run twice, once with a polyDMDAAC concentration of 100 ppm (First Run) and a second time with a polyDMDAAC concentration of 50 ppm (Second Run). A previously run microtox examination of polyDMDAAC showed that a concentration of 400 ppm is essentially non-toxic to bacteria. PolyDMDAAC was added to the experimental tank and no chemicals were added to the control tank. The water was changed on a daily basis with the old water pumped out and fresh effluent added. Fresh polyDMDAAC was added to the experimental tank with each water change. This routine was followed for a period of ten days as needed to prevent the tanks from running dry. The tanks were then monitored for an additional week or two until the presence of juvenile snails. Juvenile snails appeared three to four weeks after the first introduction of snails into the aquaria.

First Run

Snails were introduced to both control and experimental tanks on Day 1. The first egg clusters were noticed on Day 8. The addition of polyDMDAAC to the experimental tank began on Day 15; polyDMDAAC was added daily with a fresh effluent water change until Day 24, with the exception of Days 20 and 21. On Day 17 very few live snails were observed in the polyDMDAAC tank and no snails were on the underside of the blue block. This is in contrast to the control tank which had many living snails, including several on the underside of the blue block. By Day 19 there were no living snails in the polyDMDAAC tank and the egg clusters had taken on a brownish color that seemed to be a result of "floc" settling on the eggs. The control tank still had many living snails and the egg clusters were very clean and clear. The first juveniles were observed in the control tank on Day 32. The juveniles were confirmed under microscopic examination. As of Day 40, no juvenile snails were observed in the polyDMDAAC tank and the experiment was terminated (see Table 1 below).

A microscopic examination of the water from the control tank revealed a plethora of life; ciliates, rotifers, and nematodes were all observed. In contrast, an examination of the polyDMDAAC water showed little signs of life; only ciliates were observed.

Second Run

Snails were introduced to both the control and experimental tanks on Day 1. The first egg clusters were observed on Day 4. The addition of polyDMDAAC to the tank at a concentration of 50 ppm began on Day 7; polyDMDAAC was added daily with a fresh effluent water change until Day 12. On Day 9 live snails in both tanks were observed, although there were substantially fewer in the polyDMDAAC tank. On Day 15, 5 living snails in the polyDMDAAC tank and 15 in the control tank were counted. On Day 23, Juvenile snails were observed in the control tank; there were no living snails or juveniles present in the polyDMDAAC tank. A close inspection of the polyDMDAAC tank revealed only 5 "brownish" egg clusters, down from the 20 that were counted on Day 6. As of Day 28, there were still no juveniles present in the polyDMDAAC tank and the experiment was terminated (see Table 2 below).

A microscopic evaluation on Day 15 revealed life in both tanks. The control was teaming with rotifers, nematodes, ciliates, stalked ciliates, and had a loose floc. The experimental tank had fewer numbers but still plenty of rotifers, nematodes, and ciliates. The polyDMDAAC tank was much tighter than that of the control.

TABLE 1

Summary Of polyDMDAAC Experiment, 100 ppm

| Day | Control Tank | PolyDMDAAC Tank |
|---|---|---|
| 1 | Snails Introduced | Snails Introduced |
| 8 | Egg Clusters Observed | Egg Clusters Observed |
| 15 |  | Addition Of polyDMDAAC |
| 19 | Living Snails Present | No Living Snails |
| 23 | Lots Of Microscopic Life | Little Of Microscopic Life |
| 32 | Juveniles Observed | No Juveniles |

TABLE 2

Summary Of polyDMDAAC Experiment, 50 ppm

| Day | Control Tank | PolyDMDAAC Tank |
|---|---|---|
| 1 | Snails Introduced | Snails Introduced |
| 4 | Egg Clusters Observed | Egg Clusters Observed |
| 7 |  | Addition Of polyDMDAAC |
| 15 | Living Snails Present | Living Snails Present |
| 15 | Lots Of Microscopic Life | Lots Of Microscopic Life |
| 23 | Juveniles Observed | No Juveniles |

This example demonstrates that polyDMDAAC is effective in killing adult snails and in preventing snail eggs from hatching. In this example, lower levels of polymer, such as 50 ppm, seemed to be just as effective in killing the snail eggs as the higher levels, but with limited effect on the background microscopic life.

Example 3

At a waste water treatment system, a trickling filter's flow (45,000 gal.) was isolated and dosed with 13 gals of polyDMDAAC (250,000 molecular weight) (approximately 288.0 ppm). The test was run for 4.5 days. In that amount of time, there was some adult snail kill and the beginning of the egg kill process. There was no apparent effect on the bacteria.

Example 4

A full scale plant test with polyDMDAAC (250,000 molecular weight) was initiated at a waste water treatment plant. The polyDMDAAC was fed to a wet well, where it was recirculated to one isolated nitrification tower. The testing lasted between 22 & 30 days. The polyDMDAAC dosage was adjusted between 50 and 1000 ppm at various times during the test. Killing of the adult snails and egg sacks was observed.

Example 5

To determine whether snail eradication could be achieved without destroying the microbiological fauna inhabiting trickling filters and bioflocculation tanks of a waste water treatment system, various concentrations of polyDMDAAC were tested. The same Microtox procedure used to screen septage samples for toxicity, which will be known to those skilled in the art of water treatment, was used for the present example. The highest concentration tested was 500 ppm. The product was found to be non-toxic to the microbiological fauna.

Trickling Filter Simulation Experiment

The effectiveness of the present methods in an environment similar to the trickling filter towers was evaluated. To simulate this environment, several ten-gallon aquariums were set up according to the method of Example 2, as shown in FIG. 1. Each day the old primary effluent was drained and fresh primary effluent added.

Several experiments were run. Snails were added to each aquarium and given time to acclimate to the new conditions. These snails were collected from the bioflocculation tank of a waste water treatment plant by means of an auger. After about a week in the aquariums, the snails had laid several egg cases. Many snails died in this first week and were removed. After sufficient egg clusters had been laid, generally around 20, additional snails were added to each aquarium and the addition of polyDMDAAC begun. The polyDMDAAC was obtained from Calgon Corporation in liquid form.

Various concentrations of polyDMDAAC were assigned to each tank and a control was set-up. PolyDMDAAC was added to the primary effluent during the daily water changes. Periodically, the live snails were counted and egg cases examined for any change in appearance. In the lower concentrations of polyDMDAAC, 10 ppm through 100 ppm, there was no clear trend of snail death and after three weeks juvenile snails were observed in all concentrations of 100 ppm and lower (See Table 3 below).

High concentrations of polyDMDAAC, 150 ppm, 200 ppm and 300 ppm, however, were very effective. After four days, almost all snails in these concentrations were dead and the eggs had an opaque or white cloudy appearance. This condition was very different than that observed in the control, where many snails were still alive and the eggs had a clear, translucent appearance. Fifty additional snails were added to these higher concentration tanks and within two days all were dead. After four weeks of observation, the experiment was terminated. At this time there were juveniles present in the control tank but none in the 150 ppm through 300 ppm tanks.

This example demonstrates that in sufficient concentrations polyDMDAAC is effective in killing snails and preventing the development of eggs. Determining the correct concentration for each aqueous system being treated depends on the nature of the matrix. A "cleaner" sample, such as effluent, requires less polyDMDAAC than a sample with more solids, such as primary effluent. It is within the skill of those practicing in the art to determine the appropriate amount of polyquat to add to a given system to achieve effective snail control while at the same time maintain effective levels of other biological growth.

TABLE 3

Number of live snails counted at various times during experiment.

| | Concentration of polyDMDAAC | | | | | | | | |
|---|---|---|---|---|---|---|---|---|---|
| | Control | 10 | 25 | 50 | 75 | 100 | 150 | 200 | 300 | Control |
| Day 1 | 46 | 50 | 38 | 37 | 50 | 43 | 68 | 68 | 68 | 65 |
| Day 4 | 31 | 24 | 17 | 30 | 22 | 26 | 1 | 0 | 0 | 33 |
| Day 8 | 25 | 17 | 12 | 24 | 12 | 24 | 50 Additional Snails added | | | |
| Day 9 | — | — | — | — | — | — | 10 | 0 | 0 | 57 |

TABLE 3-continued

Number of live snails counted at various times during experiment.

Concentration of polyDMDAAC

| | Control | 10 | 25 | 50 | 75 | 100 | 150 | 200 | 300 | Control |
|---|---|---|---|---|---|---|---|---|---|---|
| Day 18 | 14 | 13 | 9 | 19 | 10 | 6 | 0 | 0 | 0 | 41 |
| Day 25 | Juveniles Observed In All Tanks | | | | | No Juveniles | | | Juveniles | |

"—" no reading taken

Trickling Filter Tower Experiment

PolyDMDAAC was fed to trickling filter influent at a concentration of 200 ppm for a six hour period for two consecutive days.

During the four weeks prior to polyDMDAAC addition, an average of 3267 pounds per day of snails were removed. The two weeks immediately following polyDMDAAC addition, snail removal jumped to an average of 4190 pounds per day, a 22% increase. Over the next four weeks, however, the average snail removal dropped to 2204 pounds per day, a 47% decrease (Table 4).

TABLE 4

Average Pounds Of Snails Removed

| Time | Snail Removal, lbs/day | Percent Change |
|---|---|---|
| Prior to addition | 3267 | |
| one to two weeks post-addition | 4190 | 22% Increase |
| three to six weeks post-addition | 2204 | 47% Decrease |

This example illustrates that after an initial increase in snail volume, the snail volume decreased following polyDMDAAC addition. Very heavy rains shortly after polyDMDAAC addition and the accompanying hydraulic overload may account for the 22% increase in snail removal observed in the first two weeks.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for controlling snails in an aqueous waste water biological treatment system, comprising adding to said waste water biological treatment system an effective amount of a water soluble polymer consisting of dialkyl diallyl quaternary ammonium monomers.

2. The method of claim 1, wherein said control includes one or more members selected from the group consisting of killing snails, inhibiting snail growth, preventing snail growth, inhibiting development of snail eggs, inhibiting hatching of snail eggs, and controlling the fouling potential of snails.

3. The method of claim 1, wherein said aqueous system contains snails or is prone to growth of snails.

4. The method of claim 1, wherein said waste water treatment system uses nitrifying bacteria to reduce biochemical oxygen demand, and where said water soluble polymer does not affect said nitrifying bacteria, yet kills any snails present and inhibits the development and hatching of snail eggs.

5. The method of claim 1, wherein said snails are adult snails, snail eggs, or both, and wherein said snails are submerged, partially submerged or intermittently submerged in the water of the aqueous system being treated.

6. The method of claim 1, wherein at least one of said monomers is dimethyl diallyl ammonium $X^-$, wherein $X^-$ is any suitable counterion.

7. The method of claim 6, wherein said counterion is selected from the group consisting of fluoride, bromide, chloride, hydroxide, nitrate, acetate, hydrogen sulfate and primary phosphates.

8. The method of claim 6, wherein said counterion is chloride.

9. The method of claim 1, wherein more than one polymer is added to said aqueous system.

10. The method of claim 1, wherein said effective amount is between about 0.1 and 2000 parts per million, based on total weight of active polymer and the total weight of the water in the aqueous system being treated.

11. The method of claim 1, wherein said polymer is added daily for a period of between about one and two weeks, in an amount between about 1 and 100 parts per million, based on total weight of active polymer and the total weight of the water in the aqueous system being treated.

* * * * *